United States Patent [19]

Hara et al.

[11] 4,248,949

[45] Feb. 3, 1981

[54] METHOD FOR STABILIZING ORGANIC SUBSTRATE MATERIALS INCLUDING PHOTOGRAPHIC DYE IMAGES AGAINST THE ACTION OF LIGHT AND A PHOTOGRAPHIC MATERIAL SO STABILIZED

[75] Inventors: Hiroshi Hara, Asaka; Kotaro Nakamura; Yoshiaki Suzuki, both of Minami-ashigara, all of Japan

[73] Assignee: Fuji Photo Film Co., Ltd., Minami-ashigara, Japan

[21] Appl. No.: 969,892

[22] Filed: Dec. 15, 1978

[30] Foreign Application Priority Data

Dec. 15, 1977 [JP] Japan .................. 52-151096

[51] Int. Cl.³ .............................. G03C 7/00
[52] U.S. Cl. ........................... 430/17; 430/213; 430/220; 430/372; 430/544; 430/551; 430/552; 430/554; 430/556; 430/558; 430/561; 260/429 R; 260/438.1; 260/439 R; 260/45.75 R; 8/568
[58] Field of Search ............ 96/77, 57, 114.1, 48 HD, 96/90 PC, 84 R, 84 UV, 67, 56, 99; 260/429 R, 429 AR, 429 J, 438.1, 439 R, 439 CY; 546/6

[56] References Cited

U.S. PATENT DOCUMENTS

| | | | |
|---|---|---|---|
| 3,588,216 | 6/1971 | Bloom | 260/429 R |
| 3,672,898 | 6/1972 | Schwan et al. | 96/74 |
| 3,806,462 | 4/1974 | Bloom | 260/438.1 |
| 4,050,938 | 9/1977 | Smith, Jr. et al. | 96/84 UV |

FOREIGN PATENT DOCUMENTS 1451000  9/1976  United Kingdom ............ 96/109

OTHER PUBLICATIONS

Mechanisms of Oxidative Photodegradation and of U.V. Stabilization of Polyolefins, Cicchetti, Adv. Polymer Sci., v. 7, pp. 70–111.
Research Disclosure, vol. 92, Dec. 1971, publ. 9232, pp. 107–110.
Lions et al., J.A.C.S., vol. 80, pp. 1591, 1592, 4/5/58.
Martin, J.A.C.S., vol. 80, pp. 233–236, 1/5/58.
Klviber, Inorg. Chem., vol. 4, pp. 829–833, No. 6, Jun. 1965.

Primary Examiner—Travis Brown
Attorney, Agent, or Firm—Sughrue, Rothwell, Mion, Zinn and Macpeak

[57] ABSTRACT

A method of stabilizing organic substrate materials against the action of light is disclosed wherein at least one compound represented by the following general formula (I) is made to coexist with the organic substrate material

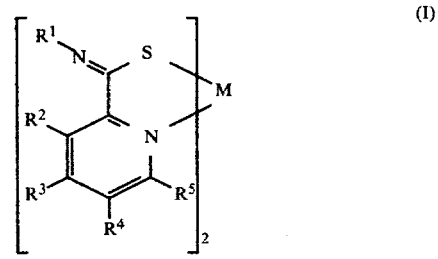

wherein M represents a Cu, Co, Ni, Pd or Pt atom, $R^1$ represents an alkyl or an aryl group, $R^2$, $R^3$, $R^4$ and $R^5$ may be the same or different and each represents a hydrogen atom, a halogen atom, an alkyl group or an aryl group. Alternatively, $R^2$ and $R^3$, $R^3$ and $R^4$ or $R^4$ and $R^5$ may combine together to form a 6-membered ring. A photographic material containing the above compound is also disclosed.

13 Claims, No Drawings

METHOD FOR STABILIZING ORGANIC SUBSTRATE MATERIALS INCLUDING PHOTOGRAPHIC DYE IMAGES AGAINST THE ACTION OF LIGHT AND A PHOTOGRAPHIC MATERIAL SO STABILIZED

BACKGROUND OF THE INVENTION

1. Field of the Invention

This invention relates to a method of stabilizing an organic substrate material against the action of light, and, more particularly, to a method for stabilizing an organic compound such as an organic dyestuff. Still more particularly, the present invention relates to a photographic material containing a specific compound to improve the light fastness of the photographic dye images.

2. Discussion of the Prior Art

As is commonly known, organic substrate materials, for example, organic dyes, tend to fade or undergo discoloration by the action of light. Accordingly, in the fields of ink technology, textile dyeing or color photography, extensive studies are being carried out in order to prevent such fading or discoloration, i.e., improve the light fastness of organic dyes. The instant invention can be applied for such purposes.

In the present specification, the term "organic substrate" or "organic substrate material" means substances which appear colored or colorless to the human eye under the illumination of sunlight and which have an absorption peak in the visible spectrum or even in the infrared region including optical whitening agent. Thus, the organic substrate materials of the instant invention include organic substances having an absorption maximum in the spectral region between about 300 nm (in the UV region) and about 800 nm (in the infrared region). These organic substrate materials occur particularly in photographic materials, e.g., color films, prints, diffusion transfer units, etc., in colored polymers useful as agricultural vinyl cover sheets, umbrellas, tents, etc.; fluorescent whitening agents; and dyed textiles, etc., and this invention is directed to improving the light fastness of these materials in each of these environments.

In the following description of the present specification, the term "dye" or "dyestuff" implies organic substances which appear colored to the human eye under the illumination of sunlight.

The word "light" in the specification means electromagnetic radiation with wavelengths up to about 800 nm, including ultraviolet light up to about 400 nm, visible light between about 400 and about 700 nm and infrared light between about 700 nm and about 800 nm.

It is widely accepted that organic substrate materials such as dyes tend to fade or change color upon exposure to light, and a large number of reports have been published on methods of retarding or reducing such fading or discoloration, i.e., of improving the light fastness of dyes. For example, U.S. Pat. No. 3,432,300 discloses one such method in which a phenol derivative having a fused heterocyclic structure is mixed with organic compounds such as indophenol, indaniline, azo and azomethine dyes to improve the fastness to visible as well as ultraviolet light.

Generally speaking, in the field of silver halide photographic materials, azomethine or indaniline type dyes are formed as the result of the reaction between the oxidation product from an aromatic primary amine developing agent and a color forming coupler, as is described in Chapter 17 of *The Theory of the Photographic Process* authored by C. E. K. Mees and T. H. James (Macmillan Co., 1967). Many methods have been proposed to improve the light fastness of the color images comprising such types of dye. Fade preventing or retarding agents conventionally used include hydroquinone derivatives disclosed in U.S. Pat. Nos. 2,360,290, 2,418,613, 2,675,314, 2,701,197, 2,704,713, 2,728,659, 2,732,300, 2,735,765, 2,710,801 and 2,816,028, U.K. Pat. No. 1,363,921, etc., gallic acid derivatives set forth in U.S. Pat. Nos. 3,457,079 and 3,069,262, Japanese Patent Publication No. 13,496/1968, etc., p-alkoxyphenols set forth in U.S. Pat. Nos. 2,735,765 and 3,698,909, chroman and coumarane derivatives set forth in U.S. Pat. Nos. 3,432,300, 3,573,050, 3,574,627, 3,764,337, 3,574,626, 3,698,909, 4,015,990, etc. However, these cited compounds can prevent fading or discoloration only to some extent but not to satisfactory degree.

Further, U.K. Pat. No. 1,451,000 discloses another method of stabilizing organic substrate materials against the action of light based on the use of an azomethine quenching compound which has an absorption maximum at a wavelength longer than that of the substrate material; unfortunately, such azomethine quenching compounds are ordinarily deeply colored by themselves, thus, adversely affecting the color phase of the substrate material.

Degradation of polymeric substances can be prevented by the use of metal chelates; reference should be made to J. P. Guillory and R. S. Becker, *J. Polym. Sci., Polym. Chem. Ed.*, 12, p. 993 (1974) and R. P. R. Ranaweera and G. Scott, *J. Polym. Sci., Polym. Lett. Ed.*, 13, p. 71 (1975). Further, a method of stabilizing dyes with metal complexes is described in Japanese Patent Application (OPI) No. 87,649/1975 (The term "OPI" as used herein refers to a "published unexamined Japanese patent application") and Research Disclosure 15162 (1976). These complexes, however, do not exhibit sufficient fade preventing capability and are poorly soluble in organic solvents. The latter property prohibits incorporating the complexes at the high concentrations required for complete fade prevention. In addition, the considerable color of these complexes deteriorates the color hue and the color purity of the substrate material when they are used in higher concentrations.

Furthermore, fade preventing agents capable of improving the light fastness of cyan dyes have not been known.

SUMMARY OF THE INVENTION

Accordingly, a principal object of the present invention is to provide a method of improving the stability of organic substrate materials against light.

Another object of the present invention is to provide a method for improving the light stability of organic substrate materials, in particular, dyes without adversely affecting on the color hue as well as color purity thereof.

Still another object of the present invention is to provide a method of stabilizing organic substrate materials against the action of light using a stabilizing agent which is readily soluble in organic solvents and which is highly compatible with the organic substrate material.

Another object of the present invention is to provide a method of stabilizing the color dyes composing color photographic images against the action of light.

Still another object of the present invention is to provide a method of stabilizing the dyestuffs resulting from the reaction of aromatic primary amine developing agents with color forming couplers against the action of light.

A further object is to improve the light fastness of colored polymers useful as agricultural vinyl sheets, umbrellas, tents, etc.

These and other objects of the present invention will become more evident from the following description of the invention.

DESCRIPTION OF THE INVENTION

All of the above-cited objects of the present invention are achieved by making at least one compound represented by the following general formula (I) coexist with an organic substrate material having an absorption peak between about 300 and about 800 nm in wavelength.

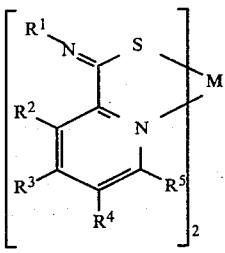

(I)

wherein M represents a Cu, Co, Ni, Pd or Pt atom; $R^1$ represents an alkyl group or an aryl group; $R^2$, $R^3$, $R^4$ and $R^5$ each represents a hydrogen atom, a halogen atom (e.g., Cl, Br, I, F), an alkyl group or an aryl group, and $R^1$, $R^2$, $R^3$, $R^4$ and $R^5$ may be the same or different, and $R^2$ and $R^3$, $R^3$ and $R^4$, or $R^4$ and $R^5$ can combine to form a non-metallic atomic group necessary to complete a 6-membered ring.

The terms "in the presence of" or "coexistant with" as used in the specification refer not only to coexistence of the substrate material and the compound of the formula (I) in the same solution, dispersion, emulsion or layer but also to the existence of the organic substrate and the complex in, for example, adjacent layers of a multilayered photographic material. As long as the complex compound is associated with the organic substrate material such that it improves the light fastness of the organic substrate, it is used "in the presence of" or "coexists" with the substrate for purposes of the present invention.

The alkyl group represented by $R^1$, $R^2$, $R^3$, $R^4$ and $R^5$ may be substituted or unsubstituted, and straight or branched chained, and preferably contain from 1 to 20 carbon atoms (excluding the carbon atoms in any substituent), including, for example, methyl, ethyl, propyl, butyl, amyl, hexyl, octyl, decyl, hexadecyl, heptadecyl, octadecyl, etc.

The aryl groups represented by $R^1$, $R^2$, $R^3$, $R^4$ and $R^5$ include substituted or unsubstituted monocyclic and bicyclic aryls, and preferably contain from 6 to 14 carbon atoms (excluding the carbon atoms in any substituent). Typical examples are phenyl and naphthyl groups.

The 6-membered ring formed by combining together $R^2$ and $R^3$, $R^3$ and $R^4$, or $R^4$ and $R^5$ is preferably a 6-membered carbocyclic ring which may be condensed with another carbocyclic aromatic ring(s) and may also be substituted with substituents as illustrated below. Representative examples of these 6-membered rings include aromatic rings, e.g., a benzene ring and a naphthalene ring.

The alkyl and the aryl groups represented by $R^1$, $R^2$, $R^3$, $R^4$ and $R^5$ and the 6-membered nuclei resulting from the connection of $R^2$ with $R^3$, $R^3$ with $R^4$, or $R^4$ with $R^5$ can contain the following substituents: a halogen atom (e.g., chlorine, bromine, iodine, etc.), a cyano group, a straight or branched alkyl group containing 1 to 20 carbon atoms (e.g., methyl, ethyl, propyl, butyl, hexyl, octyl, decyl, dodecyl, tetradecyl, hexadecyl, heptadecyl, octadecyl, methoxyethoxyethyl, etc.), monocyclic or bicyclic aryl group (e.g., phenyl, tolyl, naphthyl, chlorophenyl, methoxyphenyl, acetylphenyl, etc.) containing 6 to 14 carbon atoms, an aralkyl group (e.g., benzyl, 6-phenylhexyl, anisyl, etc.), an acyloxy group (e.g., acetoxy, benzoyloxy, p-methoxybenzoyloxy, etc.), an alkoxy group (e.g., methoxy, ethoxy, butoxy, propoxy, methoxyethoxy, etc.), an aryloxy group (e.g., phenoxy, tolyloxy, naphthoxy, methoxyphenoxy, etc.), an alkoxycarbonyl group (e.g., methoxycarbonyl, butoxycarbonyl, phenoxymethoxycarbonyl, etc.), an aryloxycarbonyl group (e.g., phenoxycarbonyl, tolyloxycarbonyl, methoxyphenoxycarbonyl, etc.), an acyl group (e.g., formyl, acetyl, valeryl, steroyl, benzoyl, toluoyl, naphthoyl, p-methoxybenzoyl, etc.), an acylamino group, (e.g., acetamide, benzamide, methoxyacetamide, etc.), an anilino group (e.g., phenylamino, N-methylanilino, N-phenylanilino, N-acetylanilino, etc.), an alkylamino group (e.g., n-butylamino, N,N-diethylamino, 4-methoxy-n-butylamino, etc.), carbamoyl group (e.g., n-butylcarbamoyl, N-(4-methoxy-n-butyl)carbamoyl, etc.), a sulfamoyl group (e.g., n-butylsulfamoyl, N,N-diethylsulfamoyl, n-dodecylsulfamoyl, N-(4-methoxy-n-butyl)sulfamoyl, etc.), a sulfonylamino group (e.g., methylsulfonylamino, phenylsulfonylamino, methoxymethylsulfonylamino, etc.), a sulfonyl group (e.g., mesyl, tosyl, methoxymethanesulfonyl, etc.), etc.; where in the above substituents, the alkyl moieties are straight or branched containing 1 to 20 carbon atoms and the aryl moieties are monocyclic or bicyclic containing 6 to 14 carbon atoms.

Among the compounds represented by the general formula (I), those which are particularly preferred for the present invention are represented by one of the following formulae (IA), (IB) and (IC).

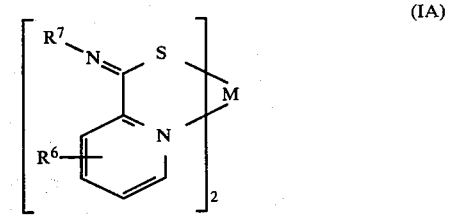

(IA)

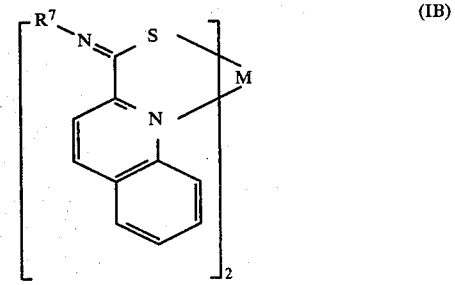

(IB)

(IB)

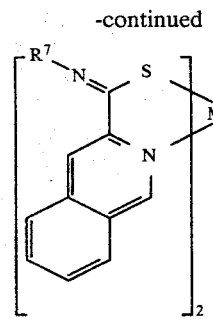

wherein M represents a Cu, Co, Ni, Pd or Pt atom, R⁶ represents a hydrogen atom, a halogen atom, an alkyl or an aryl group and R⁷ represents an alkyl or an aryl group.

As the alkyl or aryl groups represented by $R^6$ or $R^7$ in formulae (IA), (IB) and (IC), the alkyl or aryl groups defined in general formula (I) can be used favorably. Further, the alkyl or aryl groups represented by $R^6$ and $R^7$ in formulae (IA), (IB) and (IC) may be substituted by the aforementioned substituents for $R^1$, $R^2$, $R^3$, $R^4$ and $R^5$ in general formula (I).

The following structural formulae are some metal chelate complexes within formula but they are provided for the purpose of illustrating some compounds for the practice of the invention some of which are preferred, but these compounds are not to be construed as limiting the invention.

I-1
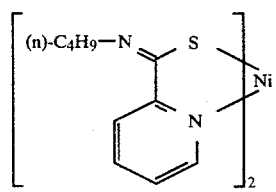

I-2
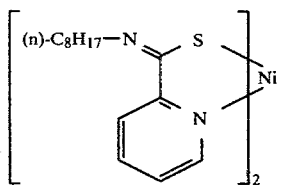

I-3
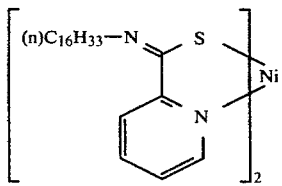

I-4
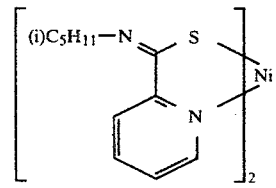

I-5
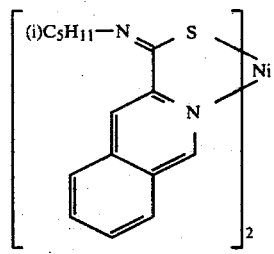

I-6
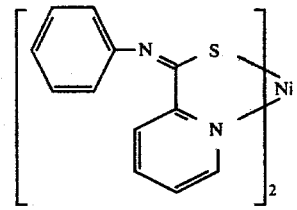

I-7
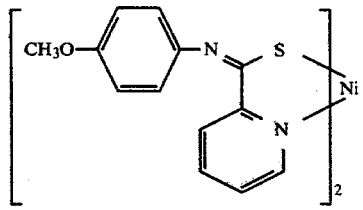

I-8
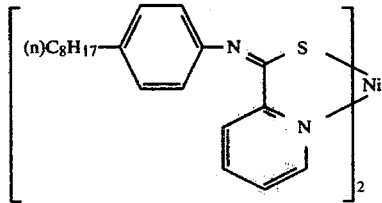

I-9
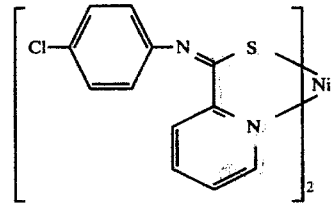

I-10
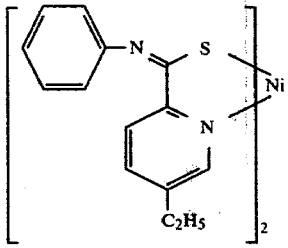

I-11
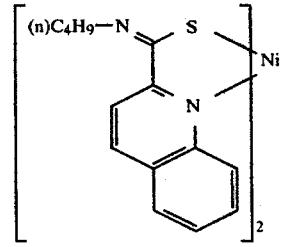

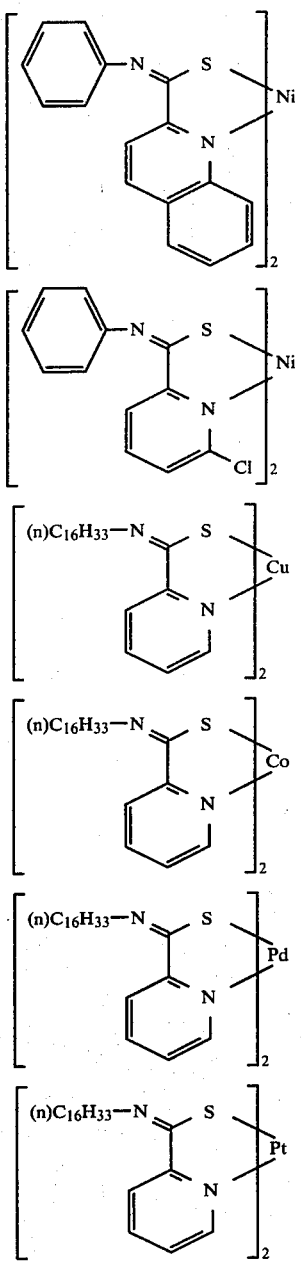

Usual methods for preparing the above-cited complexes are described in the following articles: F. Lions, K. V. Martin, *J.A.C.S.*, 80, p. 1591 (1958); K. V. Martin, *J.A.C.S.*, 80, p. 233 (1958); R. W. Kluiber, Inorg. Chem., 4, p. 829 (1954). Thiopicolineamides obtained by the reaction of amines, picoline and sulfur are added to a solution of nickel acetate tetrahydrate in a solvent mixture of water and dioxane. The mixture is heated at room temperature or refluxed for 24 hours while stirring. The crystals precipitated are separated and, if necessary, recrystallized in conventional manner.

SYNTHESIS EXAMPLE 1

Synthesis of Compound I-1

A mixture comprising 15.0 g n-butylamine, 9.3 g α-picoline and 5.0 g sulfur was heated by means of oil bath at 160° to 180° C. for 24 hours. Through distillation at reduced pressure, 15 g of N-butylthiopicolineamide with a melting point of 43° to 44° C. was obtained. After the dissolution of 1.3 g nickel acetate tetrahydrate into a mixed solvent consisting of 50 ml water and 5 ml dioxane, 1.9 g of the thus-obtained N-butylthiopicolineamide was added to the system, which was agitated for 24 hours. Compound I-1 precipitated and was separated by filtration, dried and finally recrystallized from heptane.

SYNTHESIS EXAMPLE 2

Synthesis of Compound I-6

In an oil bath kept at 160° to 180° C., a mixture comprising 18.6 g aniline, 9.3 g α-picoline, and 5.0 g sulfur was heated for 24 hours. By distillation at reduced pressure, 10 g of N-phenylthiopicolineamide was obtained (melting point: 45°–46° C.).

To a solution comprising 50 ml ethanol and 2.1 g N-phenylthiopicolineamide was added 1.3 g nickel acetate tetrahydrate dissolved in 20 ml methanol. The resulting mixture was stirred at room temperature for 2 hours. The resulting precipitate, Compound I-6, was collected by filtration, dried and recrystallized from a chloroform/ethanol mixture.

As will be apparent from the extensive discussion and examples of the organic substrate which follows, the present invention is effective with a very wide variety of organic materials, the essential point being that the substrate materials have a maximum absorption wavelength in the range of 300 to 800 nm.

The organic substrate material of the present invention includes all dyes belonging to the following classes based on dyeing property, i.e., water-soluble dyes such as basic, acid, direct, soluble vat, mordant, etc. dyes, water-insoluble dyes such as sulfur, vat, oil soluble, dispersion, azoic, oxidation, etc. dyes, and reactive dyes. These organic substrate materials include not only dyes appearing colored under the illumination of sunlight, but also colorless or pale yellow substances such as optical whitening agents.

From the viewpoint of chemical structure, the following groups of dyes are preferably used for the present invention; quinoneimine dyes (azine, oxazine, thiazine, etc.), methine and polymethine dyes (cyanine, azomethine, etc.), azo dyes, anthraquinone dyes, indamine dyes, indophenol dyes, indigoid dyes, carbonium dyes, formazane dyes, etc.

The organic substrate materials of the present invention further include image-forming dyes used in the photographic field such as those resulting from a color coupler, a DRR compound, a DDR coupler, an amidolazone compound, a dye developer, and those used in the silver dye bleach process.

The organic substrate materials to which the present invention is preferably applied are anthraquinone, quinoneimine, azo, methine, polymethine, indamine, indophenol and formazane type dyes. The types of dyes to which the present invention can be applied with particular preference are methine, polymethine, indamine and indophenol type dyes. Such methine, polymethine, indamine, and indophenol dyes include compounds containing the following moiety:

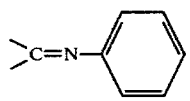

wherein the phenyl group may have substituents such as alkyl, alkoxy, halogen, amino, etc.

The dye-forming coupler suited for the practice of the present invention includes those capable of providing yellow, magenta and cyan dyes. Such couplers may be of the so-called 4-equivalent or 2-equivalent type which are disclosed, for example, in U.S. Pat. Nos. 3,277,155 and 3,458,315.

Yellow dye couplers generally contain at least one methylene group activated by a carbonyl group (e.g., open-chain ketomethylene group), and include β-diketone and β-ketoacylamide (e.g., benzoylacetanilide and α-pivalylacetanilide). Preferable couplers are set forth in, for example, U.S. Pat. Nos. 2,428,054, 4,026,706, 2,499,966, 2,453,661, 2,778,658, 2,908,573, 3,227,550, 3,253,924, 3,277,155 and 3,384,657 and U.K. Pat. No. 503,752.

Magenta dye-forming couplers suited for the practice of the present invention are exemplified by, for example, 5-pyrazolone type ones, which are set forth, for example, in U.S. Pat. Nos. 2,600,788, 2,725,292, 2,908,573, 3,006,759, 3,062,653, 3,152,896, 3,227,550, 3,252,924, 4,026,706 and 3,311,476.

Other types of magenta dye-forming couplers are indazolones described in Vittum and Weissberger, *Journal of Photographic Science*, Vol. 6, (1958), p. 158, pyrazolinobenzimidazoles set forth in, for example, U.S. Pat. No. 3,061,432, pyrazolo-s-triazole set forth in Belgian Pat. No. 724,427, and 2-cyanoacetylcoumarone set forth in, for example, U.S. Pat. No. 2,115,394.

The cyan dye-forming coupler employed in the present invention includes phenol and α-naphthol derivatives. Couplers of this type are disclosed in U.S. Pat. Nos. 2,275,292, 2,423,730, 2,474,293, 2,895,826, 2,908,573, 3,043,892, 4,026,706, 3,227,550 and 3,253,294.

In general, the above couplers are discussed in, for example, *Encyclopedia of Chemical Technology*, Vol. 5, pp. 822–825, authored by Kirk-Othmer and *Photographic Chemistry*, Vol. 2, pp. 596–614 authored by Glafkides.

As was mentioned earlier, these couplers react with the oxidation product of an aromatic primary amine silver halide developing agent to provide dyes, to which the method of the present invention is applied.

Suitable aromatic primary amine developing agents include aminophenol and phenylenediamine developers which may be used separately or in combination.

Typical examples of the developing agent capable of generating the substrate material by connecting with a variety of couplers are as follows.

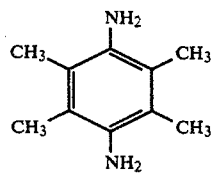

A

-continued

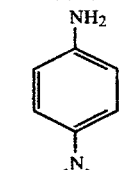

B

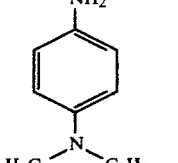

C

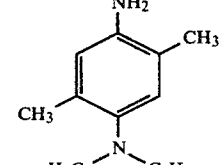

D

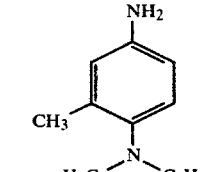

E

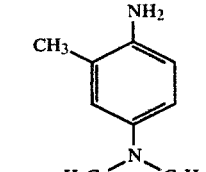

F

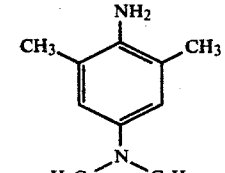

G

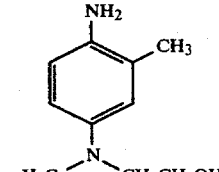

H

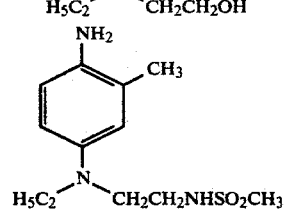

I

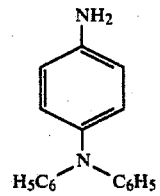

J

-continued

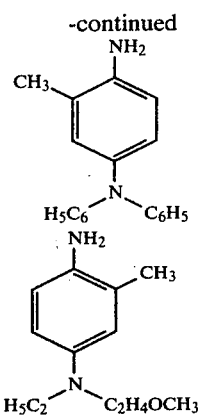

K

L

The developing agents illustrated above and others can provide organic substrates upon the reaction with photographic color couplers. Cyan, magenta and yellow couplers which are preferably employed are represented by the formulae (IIa), (IIb) or (IIc) below, respectively:

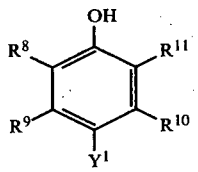 (IIa)

wherein $R^8$, $R^9$, $R^{10}$ and $R^{11}$ each represents a hydrogen atom, a halogen atom (e.g., fluorine, chlorine, bromine or iodine), an alkyl group having 1 to 20 carbon atoms (hereafter, all of the alkyl groups referred to with respect to formulae IIa, IIb and IIc may possess 1 to 20 carbon atoms) (e.g., methyl, ethyl, octyl, dodecyl, tetradecyl, octadecyl, etc.); an alkyl- or aryl-substituted carbamoyl wherein the aryl moiety has 6 to 10 carbon atoms (hereafter, all of the aryl groups referred to with respect to formulae IIa, IIb and IIc may possess 6 to 10 carbon atoms) (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R^8$ and $R^9$ may combine with each other to form a 6-membered carbocyclic ring (e.g., a benzene ring which may further be substituted with an alkyl or aryl group).

$Y^1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an aminosulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R^8$, $R^9$, $R^{10}$ and $R^{11}$, or the 6-membered ring formed by combining $R^8$ and $R^9$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di-(t)-amylphenoxy, etc.); a halogen atom (e.g., chlorine, bromine, fluorine, etc.); and the like.

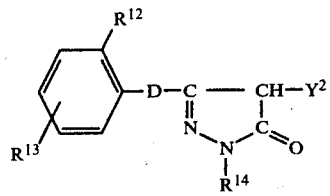 (IIb)

wherein $R^{12}$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R^{13}$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc., and $R^{14}$ represents an aryl group (e.g., phenyl, naphthyl, etc.), said alkyl and aryl groups having the number of carbon atoms discussed above with respect to formula (IIa).

D represents an amino group, a carbonylamino group, or a ureido group.

$Y^2$ represents a hydrogen atom, a halogen atom (e.g., chlorine, bromine, etc.); or a group which is releasable upon reaction with the oxidation product of a developing agent (e.g., an arylazo group, an aryloxy group, an acyloxy group, an alkylthio group, an arylthio group, etc.). Such groups are well known.

The alkyl or alkoxy group represented by $R^{12}$, the alkyl, amido, N-alkylcarbamoyl, N-alkylsulfamoyl, alkoxycarbonyl or acyloxy group represented by $R^{13}$, or the aryl group represented by $R^{14}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

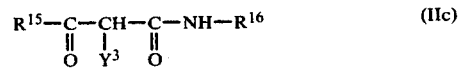 (IIc)

wherein $R^{15}$ represents an alkyl group (e.g., methyl, ethyl, (t)-butyl, (t)-octyl, etc.) or an aryl group (e.g., phenyl) and $R^{16}$ represents an aryl group (e.g., phenyl).

$Y^3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R^{15}$ and the aryl group represented by $R^{16}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc.

Couplers which can form substrate materials via the reaction with the above-cited and other developing agents are exemplified by the following compounds.

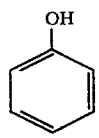

II-1

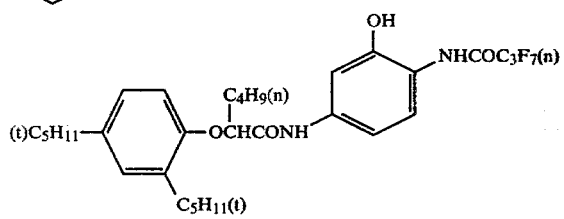

II-2

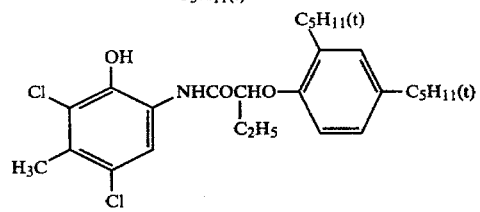

II-3

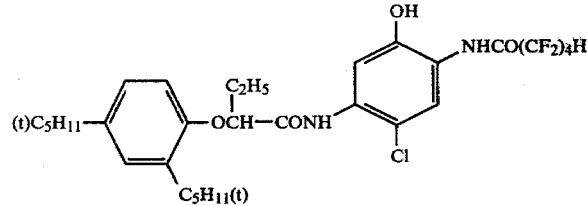

II-4

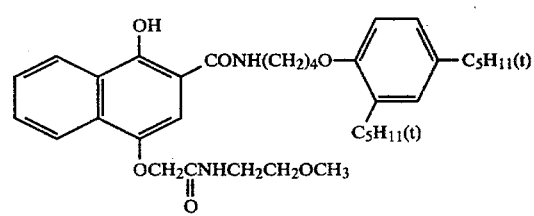

II-5

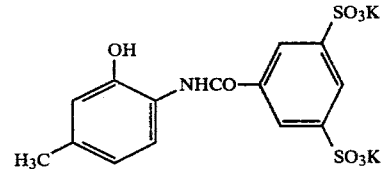

II-6

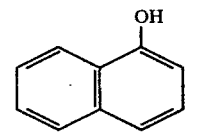

II-7

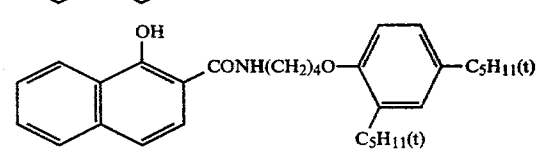

II-8

-continued
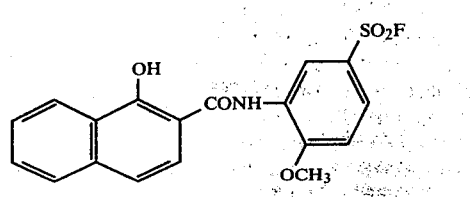
II-9
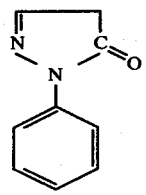
II-10
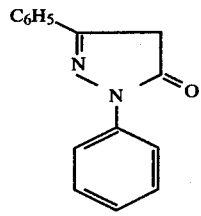
II-11
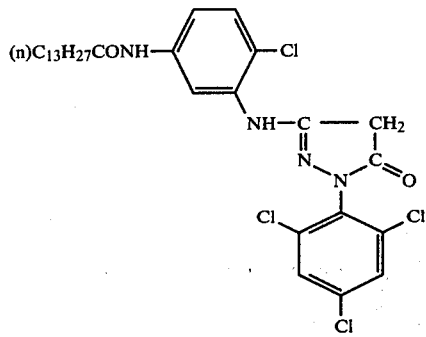
II-12
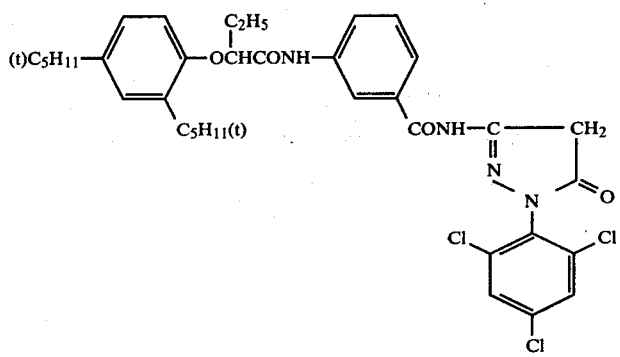
II-13
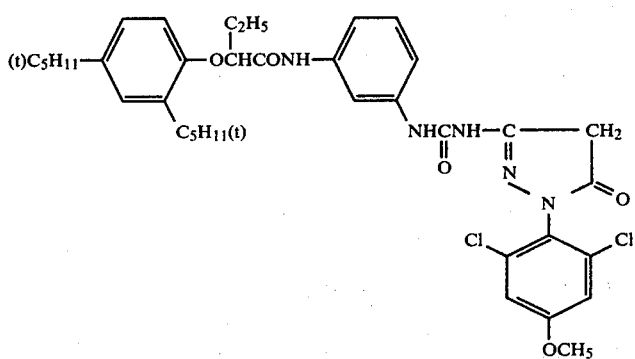
II-14

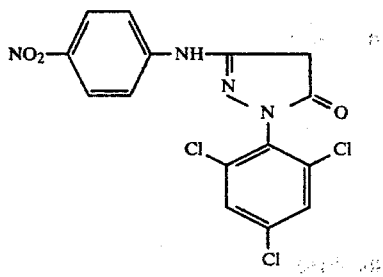
II-15
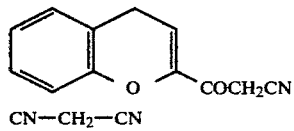
II-16
II-17
II-18
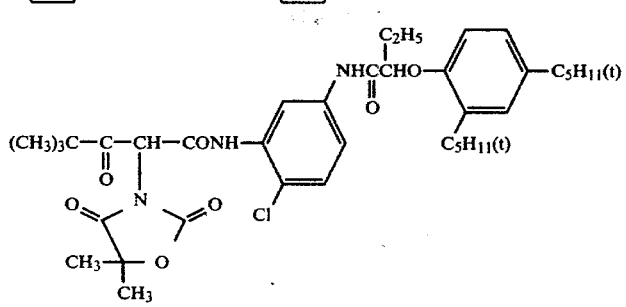
II-19
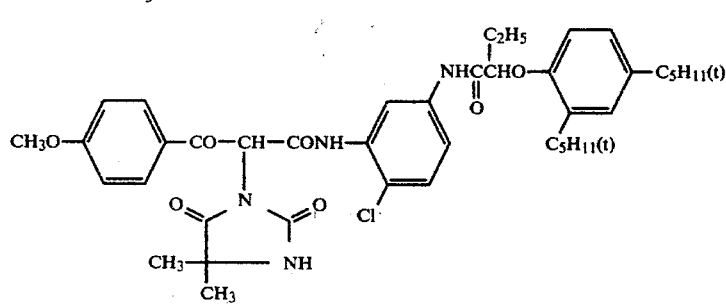
II-20
The following dyes can also be used as organic substrate material of the present invention.
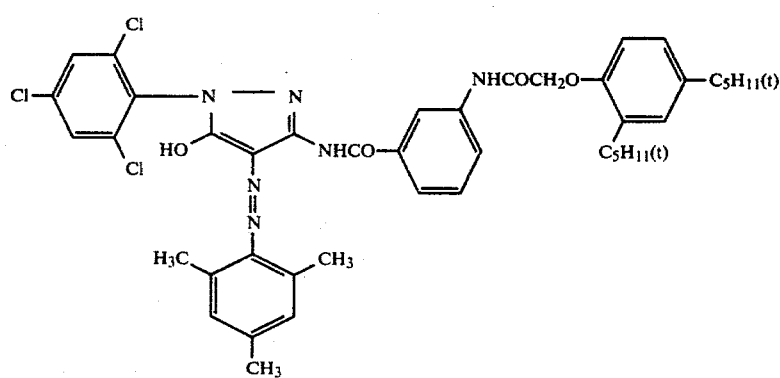
II-21

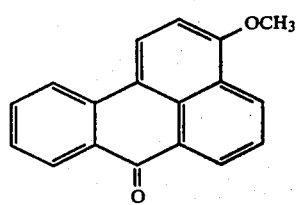
II-22
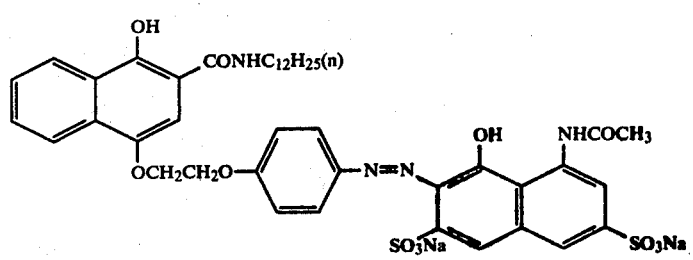
II-23
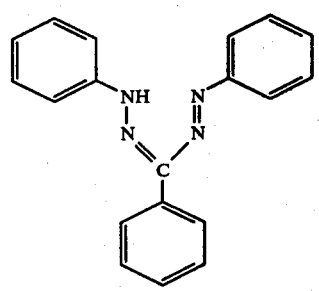
II-24
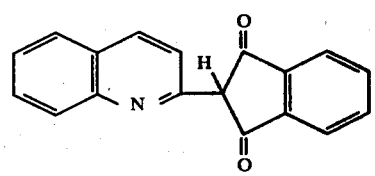
II-25
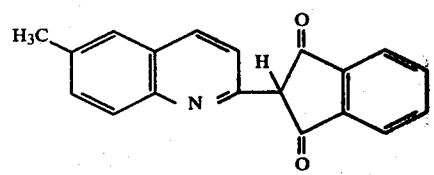
II-26
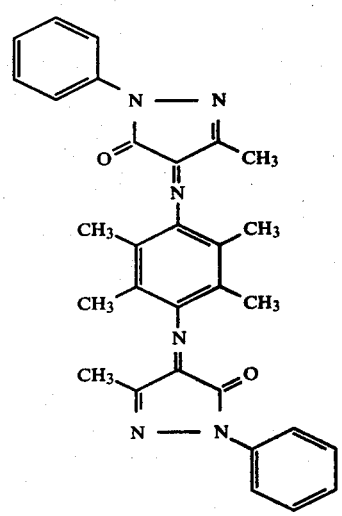
II-27

II-28
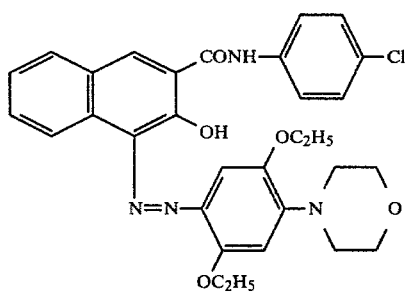
II-29
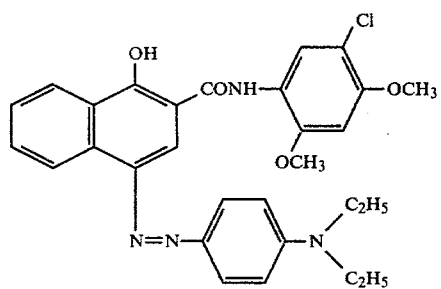
II-30
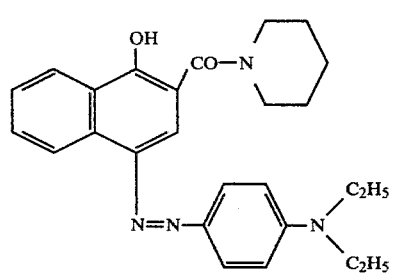
II-31
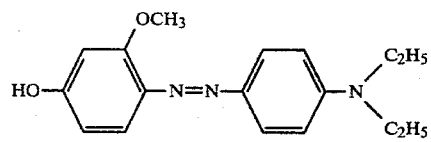
II-32
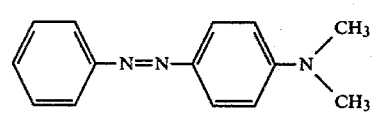
II-33
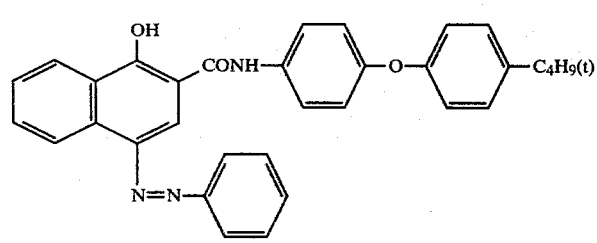
II-34
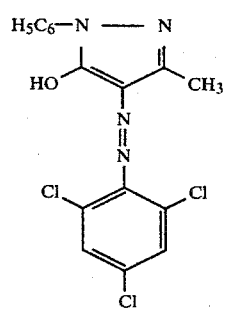

II-35
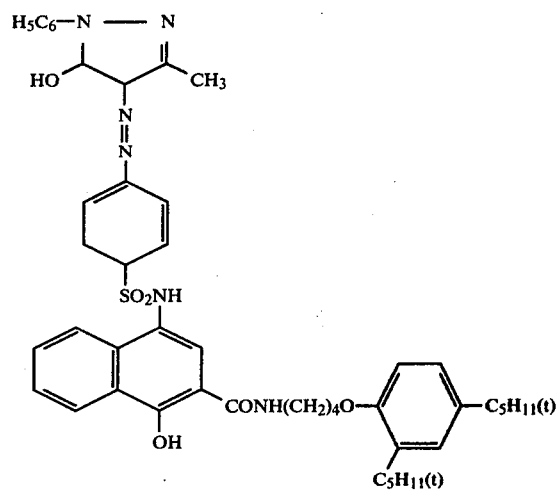
II-36
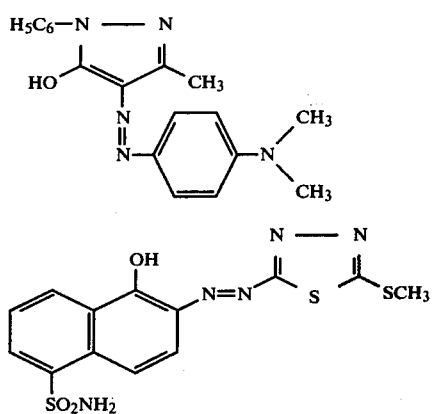
II-37
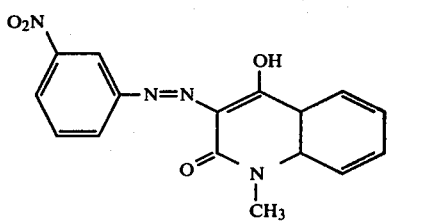
II-38
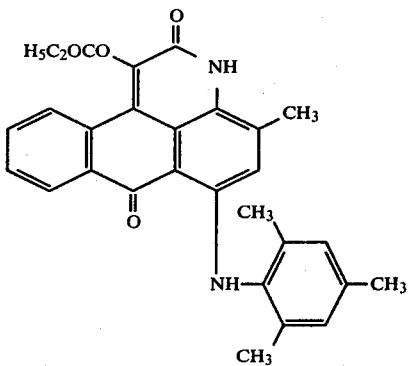
II-39
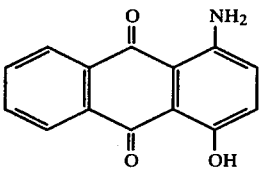
II-40

-continued
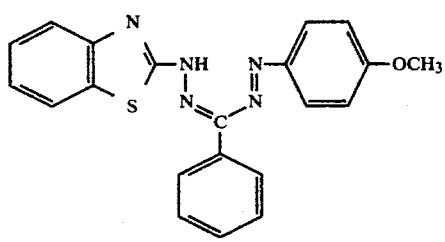 II-41
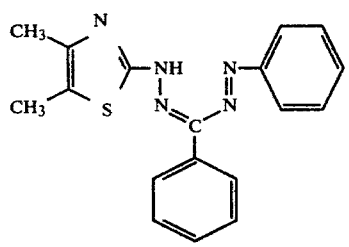 II-42
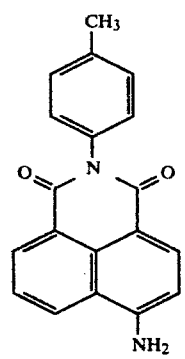 II-43
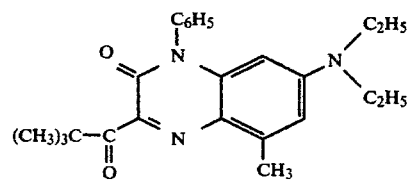 II-44
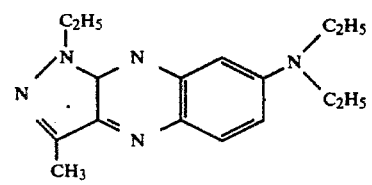 II-45
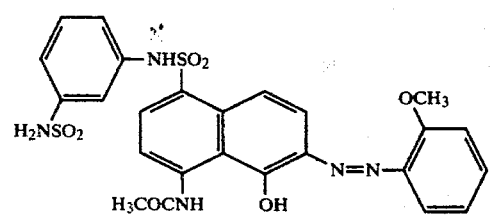 II-46

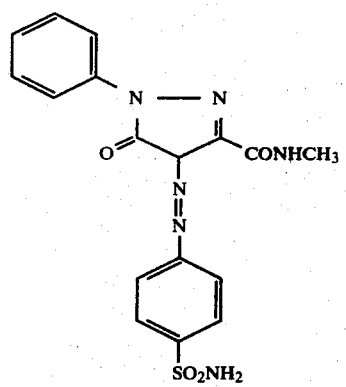
II-47
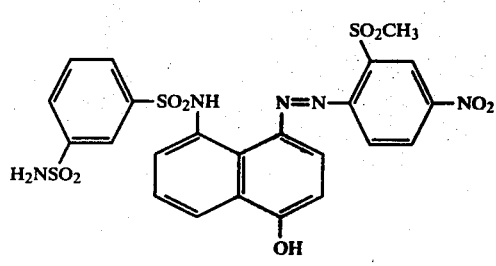
II-48
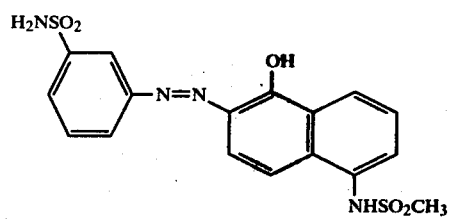
II-49
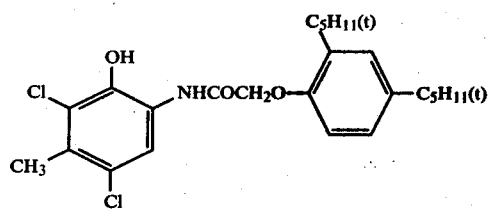
II-50
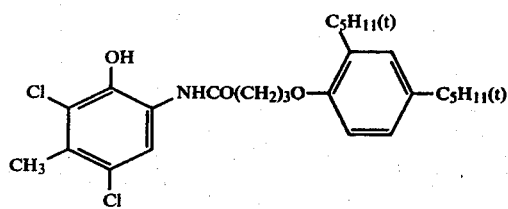
II-51
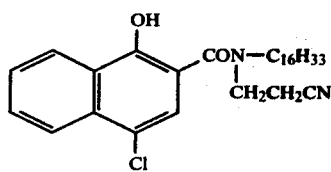
II-52
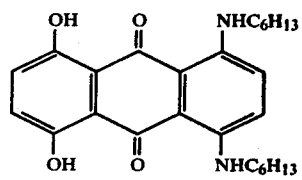
II-53

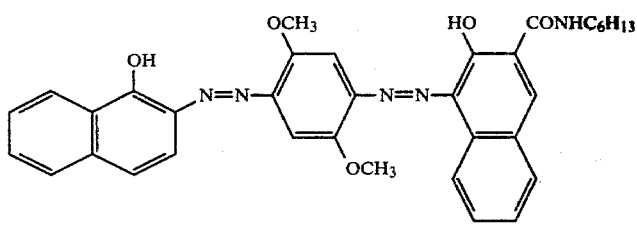
II-54
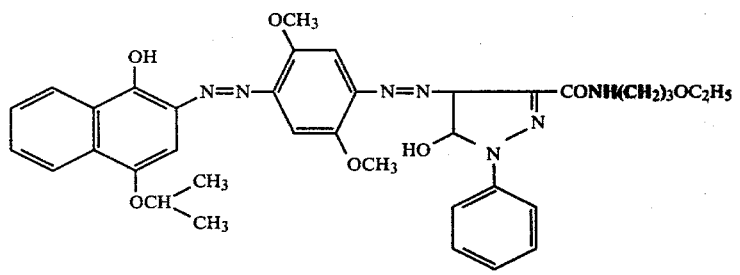
II-55
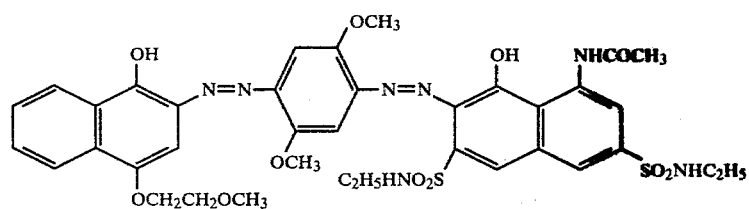
II-56
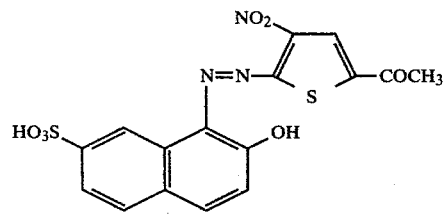
II-57
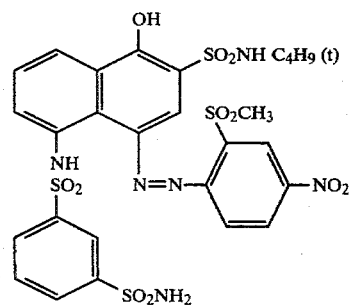
II-58
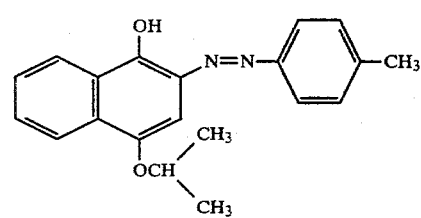
II-59
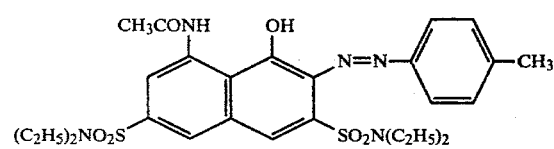
II-60

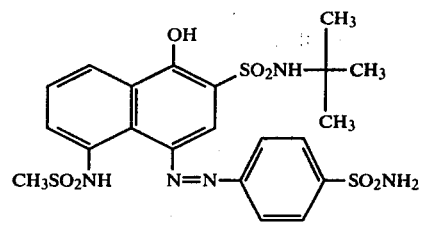 II-61
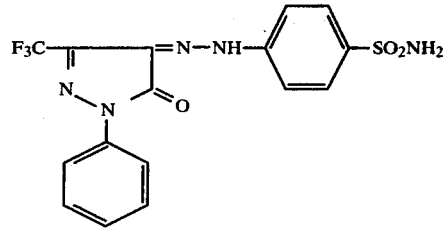 II-62
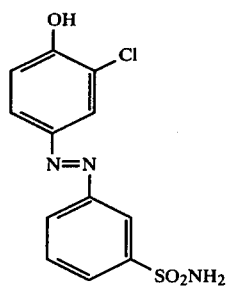 II-63
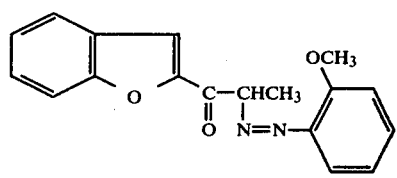 II-64
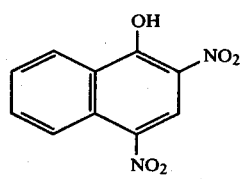 II-65
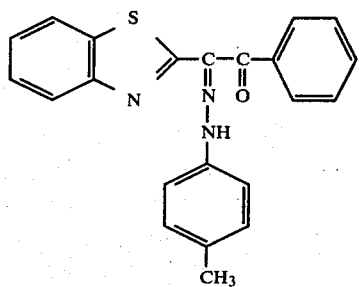 II-66
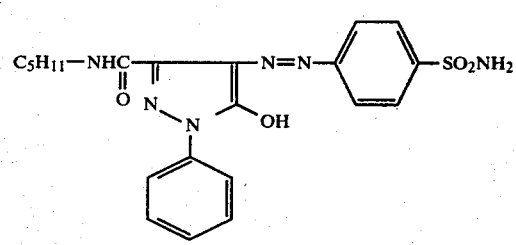 II-67

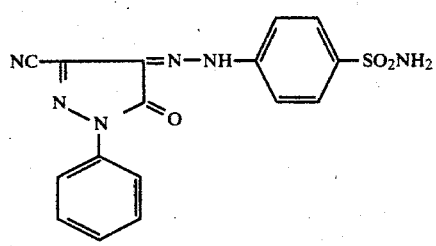

II-68

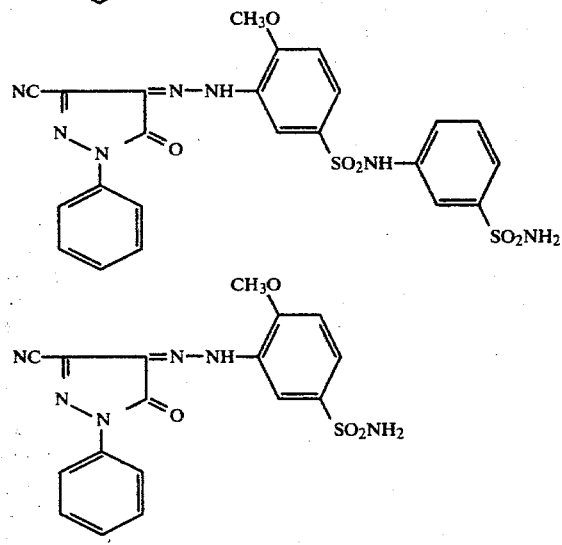

II-69

II-70

Still other types of dyes to which the present invention can be applied include those produced by the oxidation of DRR compounds which are set forth in U.S. Published Patent application B 351,673, U.S. Pat. Nos. 3,932,381, 3,928,312, 3,931,144, 3,954,476, 3,929,760, 3,942,987, 3,932,380, 4,013,635, and 4,013,633, Japanese Patent application (OPI) Nos. 113624/1976, 109928/1976, 104343/1976 and 4819/1977, Japanese Patent application No. 64533/1977 corresponding to OPI No. 149328/78, Research Disclosure Journal (1976, November), pp. 68–74, Research Disclosure, 13024 (1975), etc.

Another type of dye to which the present invention is applicable is that which is released or produced by the reaction of the oxidation product of a color developing agent with a DDR coupler, for which reference can be made to, for example, U.K. Pat. Nos. 840,781, 904,364, 932,272, 1,014,725, 1,038,331, 1,066,352 and 1,097,064, Japanese Patent application (OPI) No. 133021/1976, U.S. Defensive Publication No. T. 900,029 and U.S. Pat. No. 3,277,550.

Dye developers such as are described in Japanese Patent Publication Nos. 182/1960, 18332/1960, 32130/1973, 43950/1971 and 2618/1974, etc., can also be used in the present invention.

Various dyes used for the silver dye bleach process can also be used in conjunction with the invention. Such dyes include as yellow ones azo dyes such as Direct Fast Yellow GC (C.I. 29000), Crysophenine (C.I. 24895), etc., benzoquinone derivatives such as Indigo Golden Yellow IGK (C.I. 59101), Indigosol Yellow 2GB (C.I. 61726), Argozol Yellow GCA-CF (C.I. 67301), Indanthrene Yellow GF (C.I. 68420), Mikethrene Yellow GC (C.I. 67300), Indanthrene Yellow 4GK (C.I. 68405), etc., anthraquinone derivatives, polynuclear soluble vat dyes, and other vat dyes. Suitable magenta dyes include azo dyes such as Sumilite Supra Rubinol B (C.I. 29225), Benzobrilliant Gelanine B (C.I. 15080), etc., indigoid dyes such as Indigosol Brilliant Pink IR (C.I. 73361), Indigosol Violet 15R (C.I. 59321), Indigosol Red Violet IRRL (C.I. 59316), Mikethrene Brilliant Violet BBK (C.I. 6335), etc., soluble vat dyes comprising benzoquinone- or anthraquinone-polyheteronuclear compounds, and other vat dyes. Suitable cyan dyes include azoic ones such as Direct Sky Blue 6B (C.I. 24410), Direct Brilliant Blue 2B (C.I. 22610), Sumilite Supra Blue G (C.I. 34200), etc., phthalocyanine ones such as Sumilite Supra Turkey Blue G (C.I. 74180), Mikethrene Brilliant Blue 4G (C.I. 74140), etc., Indanthrene Turkey Blue 5G (C.I. 69845), Indanthrene Blue GCD (C.I. 73066), Indigosol 04G (C.I. 73046), Anthrasol Green IB (C.I. 59826), etc.

While the mechanism whereby the complex of the present invention improves light fastness is not entirely clear, it is believed that upon exposure to light the organic substrate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention effectively improves the light fastness of the organic substrate.

As described above, the metal chelate complexes characterizing the present invention function to stabilize the organic substrate materials. Such complex compounds can be present in one of the emulsion layers of a color photographic film or throughout all the layers thereof. They may further be incorporated in any elementary layer involved in the light-insensitive portions composing a color transfer material. The complex can be added to the hydrophilic colloids composing the photographic layers in the form of a solution using a volatile organic solvent or a water-miscible organic solvent which does not adversely affect the photographic properties of the resulting photographic layer, such as an alcohol (methanol, ethanol, isopropyl alcohol, butanol, etc.), an ether (dimethyl ether, ethyl methyl ether, diethyl ether, 1-ethoxypropane, etc.), a glycol (1,2-ethanediol, 1,2-propanediol, 1,3-propanediol, etc.), a ketone (acetone, ethyl methyl ketone, 3-pentanone, etc.), an ester (ethyl formate, methyl acetate, ethyl acetate, etc.), an amide (formamide, acetamide, succinamide, etc.), etc. Addition of the complex should preferably be carried out during the manufacture of silver halide photographic emulsion, the dispersion of couplers or the preparation of the coating composition prior to preparing the photographic coating.

For the introduction of such a complex into the hydrophilic colloid of the photographic coating, methods commonly employed for the dispersion of photographic couplers may be used. As an example, U.S. Pat. Nos. 2,304,939 and 2,322,027 disclose the use of low volatile organic solvents for the dissolution of couplers. Other methods applicable to the present purpose are disclosed in U.S. Pat. Nos. 2,801,170, 2,801,171 and 2,949,360 wherein highly volatile or water-miscible organic solvents are employed together with high boiling point ones.

Examples of high boiling point organic solvents which are effective for dispersing the organic substrate materials as well as the metal complexes involved in the present invention include di-n-butyl phthalate, benzyl phthalate, triphenyl phosphate, tri-o-cresyl phosphate, diphenylmono-p-tert-butylphenyl phosphate, monophenyldi-p-tert-butylphenyl phosphate, diphenylmono-o-chlorophenyl phosphate, monophenyldi-o-chlorophenyl phosphate, 2,4-di-n-amylphenol, 2,4-di-t-amylphenol, N,N-diethyllaurylamide, trioctyl phosphate and thihexyl phosphate, the latter two being set forth in U.S. Pat. No. 3,676,137.

Volatile or water-miscible organic solvents which can be advantageously used together with the above-cited low volatile organic solvents are disclosed in, for example, U.S. Pat. Nos. 2,801,171, 2,801,170 and 2,949,360.

These organic solvents include:

(1) those with lower boiling points and substantially immiscible with water such as, for example, methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride, chloroform, etc., and (2) Water-miscible ones such as, for example, methyl isobutyl ketone, $\beta$-ethoxyethyl acetate, $\beta$-butoxytetrahydrofurfuryl adipate, diethyleneglycol monoacetate, methoxytriglycol acetate, acetonylacetone, diacetone alcohol, ethylene glycol, diethylene glycol, dipropylene glycol, acetone, methanol, ethanol, acetonitrile, dimethylformamide, dioxane, etc.

In general, the complex of the formula (I) is dissolved or suspended in an appropriate solvent which is chosen depending upon the physical properties of the complex used from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc., together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

In the case of a photographic material, the substrate material (the dye image) and the complex each may be present in one or more of the hydrophilic colloid layers making up the photographic element (film, paper, diffusion transfer unit, etc.). It is preferred that the metal chelate complex and the organic substrate material be present (i.e., coexist) in the same emulsion layer, of course, the effects of the present invention can also be accomplished when the complex and substrate are present in contiguous layers as long as diffusion is allowed to occur between the layers. Were any (further) undesirable diffusion to occur, conventional mordanting techniques could be applied to the present invention. In the case of incorporating the complex into a silver halide emulsion layer, the complex can be incorporated into each emulsion layer making up the photographic element. In this case, the total amount of complex is present in the amounts set forth below. The complex and substrate may be present in non-light sensitive elements or layers as well, such as the dye image-receiving layer used in diffusion transfer film units. In the case of image transfer units, the metal chelate complex is preferably located in a layer where dye images are finally found, i.e., in an image-receiving layer. Usually, the dye images formed in the image-receiving layer do not diffuse further into any other layer(s) so that the complex is easily maintained in the vicinity of the dye. When the substrate material and the complex are contained in a nonlight-sensitive image recording elements, the substrate material is preferably mordanted. Accordingly, in such a case, the complex possesses a ligand that is capable of retaining it within the mordanted layer of the image-receiving element so as not to diffuse away from the vicinity of dye to be stabilized.

A number of types of image transfer film units are particularly appropriate for the practice of the present invention. One is the imbibition transfer film unit set forth in U.S. Pat. No. 2,882,156. The present invention can be further used in conjunction with the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Pat. Nos. 757,959 and 757,960.

The complex and the substrate material concerning the present invention can be used together with the compounds described in *Product Licensing Index*, Vol. 92 (1971, Dec.), No. 9232, pp. 107–110, according to the methods described therein.

Any amount of the complex will bring about some improvement in the light fastness of the organic substrate and theoretically there is no upper limit for the amount of the complex. Preferably, the complex is present in an amount of at least 0.1 mol% based on 1 mol of the organic substrate material, more preferably in an amount of 0.1 to 1,000 mol%, and most preferably in an amount of 1 to 300 mol%. In the case of a photographic material, the amount is often expressed in a weight unit per square meter of photographic material which can be calculated from the parameters set out above. For convenience, however, in the case of a photographic material, the complex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology. As is well known to those skilled in the art, the substrate material is preferably present in the range of from about 10 to $10^4$ micromoles per square meter of the photographic material. A more preferable range is from about 100 to about $3 \times 10^3$ micromoles per square meter of the photographic product.

The substrate material of the present invention usually has a maximum absorption peak at a wavelength shorter than about 800 nm, and preferably between about 300 and 800 nm, and more preferably between about 400 and 800 nm.

In the photographic material based on the present invention, any material ordinarily used as the support for photographic products can be used in this invention. Examples thereof are cellulose nitrate films, cellulose acetate films, cellulose acetate/butyrate films, cellulose acetate/propionate films, polystyrene films, poly(ethylene terephthalate) films, polycarbonate films, laminated products comprising these films, papers, etc. Other suitable support materials include baryta paper, papers coated or laminated with an α-olefin polymer such as, in particular, polyethylene, polypropylene and other $C_2$–$C_{10}$ α-olefin polymers, plastic films set forth in Japanese Patent Publication No. 19068/1972 having a roughened surface in order to improve adhesion to other polymeric materials, etc.

For the photographic light-sensitive materials used in the present invention, a number of hydrophilic colloids are employed as the binder for the photographic emulsion coating or for other elementary coatings composing the photographic product. Such hydrophilic colloids include, for example, gelatin, colloidal albumin, casein, carboxymethylcellulose, hydroxyethylcellulose and other cellulose derivatives, carbohydrate derivatives such as agar-agar, sodium alginate, starch and its derivatives, etc., synthetic hydrophilic colloids such as poly(vinyl alcohol), poly(N-vinylpyrrolidone), acrylic acid containing copolymers, maleic anhydride containing copolymers poly(acrylamide), derivatives and partially hydrolyzed products therefrom, etc. According to particular requirements involved, two or more of these colloids can be combinedly used in proviso that they are mutually compatible.

The most widely used among these is gelatin, which can be replaced partially or wholly with synthetic polymeric materials or so-called gelatin derivatives. Gelatin derivatives can be prepared by treating or modifying gelatin with a reagent having a functional group capable of entering into reaction with the functional groups contained in the gelatin such as an amino, an imino, a hydroxy, and a carboxy group, or grafting a polymer chain to the gelatin molecule.

The photographic emulsion and other additional coatings concerning the present invention can contain synthetic polymer materials such as water-dispersible vinyl polymers in the form of latex (for example, materials which can improve the dimensional stability of the resulting photographic product in particular), alone or in combination with other polymers or with a hydrophilic, water-permeable colloid.

The silver halide photographic emulsion used in the present invention can be prepared by mixing a water-soluble silver salt (e.g., silver nitrate) with a water-soluble halide (e.g., potassium bromide), each in the form of solution, under the presence of a water-soluble polymer material such as gelatin. Suitable silver halides include silver chloride, silver bromide, and silver mixed halides such as chlorobromide, iodobromide, chloroiodobromide, etc. Silver halide grains are prepared by any method conventionally known in the art including the so-called single and double jet methods, and the control double jet method. Further, two or more silver halide photographic emulsions each independently prepared may be blended.

To such a photographic emulsion, one can incorporate various compounds for the purpose of preventing sensitivity lowering or generation of fog during manufacturing steps, storage or during processing. Typical compounds include various heterocyclic compounds such as 4-hydroxy-6-methyl-1,3,3a,7-tetrazaindene, 3-methyl-benzothiazole, 1-phenyl-5-mercaptotetrazole, etc., Hg containing compounds, mercapto compounds, metal salts, etc.

The silver halide emulsion associated with the present invention can be chemically sensitized according to any known methods. Suitable chemical sensitizers include chloroaurates, auric trichloride, and other gold compounds, salts of noble metals such as Pt, Pd, Ir, Rd, etc., sulfur compounds like sodium thiosulfate which are capable of providing silver sulfide via reaction with silver salts, various reducing compounds such as stannous salts, organic amines, etc.

If necessary, the photographic emulsion associated with the present invention may be spectrally sensitized with the individual or combined use of cyanine dyes such as cyanine, merocyanine or carbocyanine dyes, etc., and styryl dyes. The choice of dye depends on the wavelength region to be sensitized, the expected level of photographic speed, the purpose and applications intended for the finished product, etc.

The hydrophilic colloid layer involved in the photographic product concerning the present invention may be crosslinked using various hardening agents. Suitable hardening agents include, for example, aldheyde compounds, active halogen compounds, vinylsulfone compounds, carbodiimide compounds, N-methylol compounds, epoxy compounds, etc.

One preferred embodiment of the present invention will be described in which the present method is applied to a color photographic product.

The color photographic product is imagewise exposed and processed in a conventional manner to form dye images. The processing usually comprises color development, bleach, and fix, to which water-washing or stabilization are added according to individual requirement. In some cases, two elementary steps may be united, one typical example being the unification of bleach and fix to a single bath. Color development is usually performed in an alkaline solution containing an aromatic primary amine developing agent. Suitable aromatic primary amine developing agents have been shown by structural formulae of from (A) to (L).

In case where the present invention is applied to a diffusion transfer color film unit as another embodiment of this invention, the processing of the exposed emulsion is achieved automatically inside such unit. The developing agent is contained in a rupturable container. In addition to Compounds (A) to (L) illustrated earlier, N-methylaminophenol, 1-phenyl-3-pyrazolidone, 1-phenyl-4,4-dimethyl-3-pyrazolidone, 1-phenyl-4-methyl-hydroxymethyl-3-pyrazolidone, 3-methoxy-N,N-diethyl-p-phenylenediamine, etc., are also suitable as developing agents.

Any of the following processes can be employed to develop a color image in the photographic product associated with the present invention: the coupling reaction between a dye forming color coupler and the oxidation product from a chromogenic developing agent comprising p-phenylenediamine; development with a dye developer, the oxidative degradation of a DRR compound, the dye releasing reaction upon coupling of a DDR coupler, the dye formation reaction upon coupling of a DDR coupler, a silver dye bleach process, and the like.

Thus, the present invention can be applied to various types of photographic light-sensitive products including color positive film, color printing paper, color negative film, color reversal film, a diffusion transfer color film unit, a silver dye bleach photographic product, etc.

EXAMPLE 1

Into a mixture comprising 3 ml tricresyl phosphate and 5 ml ethyl acetate was dissolved 0.1 g of 1-(2,4,6-trichlorophenyl)-3-(2-chloro-5-tetradecaneamide)anilino-4-[4-(N-ethyl-N-β-methanesulfonamidoethyl)amino-phenylimino]-5-oxo-2-pyrazoline. This solution was dispersed into 10 g of a 10% gelatin solution containing 1 ml of 1% sodium dodecylbenzenesulfonate aqueous solution. The resulting emulsified dispersion was then coated on a support comprising paper substrate the surfaces of which were laminated with polyethylene film and dried as Sample A.

In a similar manner Sample B was prepared by adding 20 mg of Compound I-1 of the present invention into the emulsified dispersion. Samples C and D were prepared by using 2,5-di-tert-octylhydroquinone as a conventionally known fade-preventing agent in the amounts of 25 and 250 mg, respectively. The coating rate of the dye was 60 mg/m² for every sample. In sample B, the coated amount of Compound I-1 was 12 mg/m² and in Samples C and D, the coated amount of the octylhydroquinone was 15 mg/m² and 150 mg/m², respectively. A 48 hour fading test was performed on each of these samples in a xenon tester loaded with a UV cut filter C-40 (a product of the Fuji Photo Film Co.) at a light intensity of 200,000 luxes. The optical density was measured with a Macbeth Densitometer RD 514 loaded with a green filter of status AA. The results are shown in Table I.

TABLE I

| Sample | Initial Density | Density after Fading Test |
| --- | --- | --- |
| A | 0.81 | 0.03 |
| B | 0.81 | 0.69 |
| C | 0.82 | 0.15 |
| D | 0.81 | 0.32 |

The results in Table I show the excellent light fastness which accompanies the incorporation of Compound I-1 characterizing the present invention. Samples C and D show a far poorer light stability effect in comparison to Sample B, though 2,5-di-tert-octylhydroquinone is contained in Sample C at the same molar concentration as that of Compound I-1 in Sample B, and for Sample D in a higher concentration by the factor of ten.

EXAMPLE 2

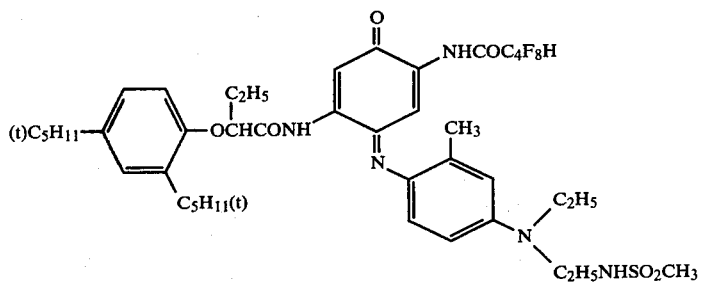

A solution prepared by dissolving 0.1 g of a dye having the structural formula shown above into a mixture of 3 ml dibutyl phthalate and 5 ml ethyl acetate was emulsified into 10 g of a 10% aqueous gelatin solution containing 1 ml of a 1% sodium dodecylbenzenesulfonate solution. Then, this emulsified dispersion was coated on a support comprising a paper substrate laminated with polyethylene film on both surfaces, and the coated sheet was dried to give Sample E.

By repeating the procedure, Sample F was prepared by further adding 30 mg of Compound I-7 characteristic of the present invention to the emulsified dispersion to provide a coating amount of Compound I-7 of 15 mg/m², Sample G was prepared by adding 100 mg of α-tocopherol, a conventional fade preventing agent for dyes, to provide a coating amount of 50 mg/m². The coating rate of dye was 50 mg/m² for every sample. A 48 hour fading test was performed on each of these samples in a xenon tester loaded with a UV cut filter C-40 (a product of the Fuji Photo Film Co.) at a light intensity of 200,000 luxes. The density measurements were carried out with a Macbeth Densitometer Type RD 514 loaded with a Status AA red filter. The results are summarized in Table II.

TABLE II

| Sample | Initial Density | Density after Fading Test |
|---|---|---|
| E | 0.89 | 0.21 |
| F | 0.91 | 0.63 |
| G | 0.91 | 0.24 |

The results show the excellent fade preventing effect of Compound I-7 characterizing the present invention. This fact is truly significant when the lack of any satisfactory fade preventing agent for ordinary cyan dyes is considered.

EXAMPLE 3

Into a mixture comprising 30 ml tricresyl phosphate, 5 ml dimethylformamide and 15 ml ethyl acetate was dissolved 10 g of a magenta coupler, 1-(2,4,6-trichlorophenyl)-3-[(2-chloro-5-tetradecaneamido)anilino]-2-pyrazoline-5-one. The resultant solution was emulsified in 80 g of a 10% aqueous gelatin solution containing 8 ml of a 1% sodium dodecylbenzenesulfonate.

A coating mixture was prepared by blending this emulsified dispersion with 145 g of green sensitive silver chlorobromide emulsion (Br content: 50 mol%, Ag content: 7 g), and further adding sodium dodecylbenzenesulfonate as a coating aid. The mixture was coated on a support comprising a paper substrate the surfaces of which were laminated with polyethylene. The coating rate of coupler for the thus-prepared Sample H was 400 mg/m².

By repeating the procedure, Sample I was prepared by further adding Compound I-3 characteristic of the present invention in an amount of 3.8 g to provide a coating amount of 152 mg/m² while Sample J was prepared using 1.6 g of 2,5-di-tert-octylhydroquinone, a conventional fade preventing agent for dyes, to provide a coating amount of the octylhydroquinone of 64 mg/m². After 1 second exposure of 1,000 lux light, each sample was processed with the following processing solutions.

| Developer: | |
|---|---|
| Benzyl alcohol | 15 ml |
| Diethylenetriamine pentaacetic acid | 5 g |
| KBr | 0.4 g |
| Na₂SO₃ | 5 g |
| Na₂CO₃ | 30 g |
| Hydroxylamine sulfate | 2 g |
| 4-Amino-3-methyl-N-ethyl-N-β-(methanesulfonamido)ethylaniline . 3/2 H₂SO₄. H₂O | 4.5 g |
| Water to make | 1 l |
| pH | 10.1 |
| Blix Bath: | |
| Ammonium thiosulfate (70 wt%) | 150 ml |
| Na₂SO₃ | 5 g |
| Na[Fe(EDTA)] | 40 g |
| EDTA | 4 g |
| Water to make | 1 l |
| pH | 6.8 |

| Processing Conditions: | Temperature | Period |
|---|---|---|
| Development | 33° C. | 3 min 30 sec |
| Blix | 33° C. | 1 min 30 sec |
| Rinse | 28 to 35° C. | 3 min |

Each sample thus-processed and provided with a dye image was exposed to sunlight through a UV cut filter C-40, a product of the Fuji Photo Film Co., eliminating radiation shorter than 400 nm in wavelength, for 2 weeks. The density changes in an area having an initial density of 2.0 is shown in Table III. The density was measured with a Macbeth Densitometer Type RD-514 loaded with a Status AA filter.

TABLE III

| Sample | Density after Sunlight Radiation at an Area of Initial Density of 2.0 | Residual Rate of Dye* (%) |
|---|---|---|
| H | 0.79 | 39.5 |
| I | 1.84 | 92.0 |
| J | 1.38 | 69.0 |

*Calculated according to the following formula:
Residual rate of dye = (Density after sunlight radiation/2.0) × 100

From these data, one can see that Compound I-3 is an efficient fade preventing agent.

EXAMPLE 4

A solution of 15 mg of a dye having the structure below and 500 mg of polycarbonate, Lexan 145 (trade name, manufactured by General Electric Co., Ltd.) in 100 ml of dichloromethane was coated onto a glass plate using a spinner. A magenta-colored film of 5.5μ thickness was thus prepared as Sample K.

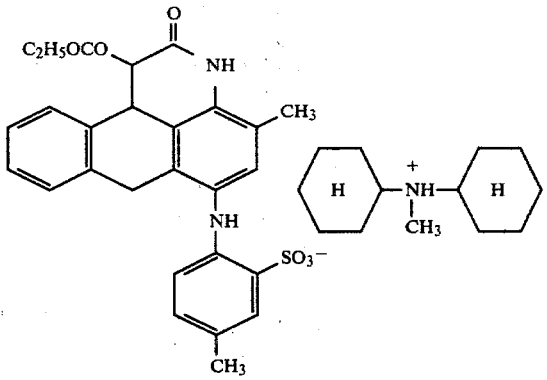

In a similar manner, five kinds of colored films were prepared as Samples L, M, N, O and P except that Compounds I-3, I-14, I-15, I-16 and I-17 were further incorporated in the solution, respectively.

The coating rate of the dye and the fade prevention compounds were 500 mg/m² and 50 mg/m², respectively.

The thus-obtained films were exposed to sunlight for 1 month and a color fading test was carried out. The results obtained are shown in Table IV below, in which density was measured at 550 nm.

TABLE IV

| Sample | Initial Density | Density after Fading |
|---|---|---|
| K | 1.0 | 0.50 |
| L | 1.0 | 0.85 |
| M | 1.0 | 0.80 |
| N | 1.0 | 0.75 |
| O | 1.0 | 0.85 |
| P | 1.0 | 0.70 |

From the results shown in Table IV, it can be clearly seen that color fade is markedly prevented in the samples containing the compounds of the present invention, in particular, the effect is excellent when the chelate metal is Ni, Pd or Cu.

Briefly summarizing the effects achieved by the metal chelate complex employed in the present invention:

(1) The metal chelate complex is readily soluble in organic solvents.

(2) In addition, the structure of the chelate complex can easily be modified so that it permits a large latitude for obtaining desired solubility.

(3) As a result of the latitude of its solubility, the complex is readily enveloped in oiled droplets and as a result, photographically undesired interaction with silver halide (e.g., desensitization) is avoidable.

(4) Due to its extremely high solubility, a small amount of the complex is sufficient to effect light fastness, conversely, a large amount can also be employed as in the case of umbrellas, agricultural vinyl cover sheets, etc.

(5) Where the chelate is used in a photographic element, no adverse effect on photographic properties is encountered.

(6) The complex is the first fading prevention agent suitable for improving the light fastness of cyan dye images.

For the reasons above, the metal chelate complex used in the present invention provides excellent light fastness.

While the invention has been described in detail and with reference to specific embodiments thereof, it will be apparent to one skilled in the art that various changes and modifications can be made therein without departing from the spirit and scope thereof.

What is claimed is:

1. A method of stabilizing a photographically useful organic substrate material having an absorption peak between about 300 and about 800 nm in wavelength, said organic substrate material being selected from the group consisting of anthraquinone dyes, quinoneimine dyes, azo dyes, methine dyes, polymethine dyes, indamine dyes, indophenol dyes, indigoid dyes, carbonium dyes and formazane dyes, against the action of light which comprises making coexist with said substrate material at least one compound represented by the following general formula (I)

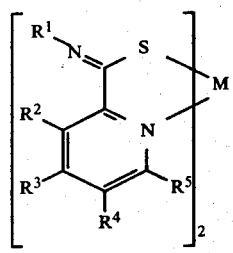

(I)

wherein M represents a Cu, Co, Ni, Pd or Pt atom; $R^1$ represents an alkyl group or an aryl group; $R^2$, $R^3$, $R^4$ and $R^5$ may be the same or different and represent a hydrogen atom, a halogen atom, an alkyl group or aryl group; and further, $R^2$ and $R^3$, $R^3$ and $R^4$ or $R^4$ and $R^5$ may combine to form a 6-membered ring, said compound of the formula (I) being present in a stabilizing amount which does not adversely affect color hue as well as color purity of the photographically useful organic substrate material.

2. The method of claim 1, wherein said organic substrate is a color photographic dye image produced from dye-forming couplers, DDR couplers, DRR compounds, amidrazone compounds, dye developers or dyes employed in a silver dye bleach process.

3. The method of claim 1, wherein said metal complex salt is represented by the formula (IA), (IB) or (IC):

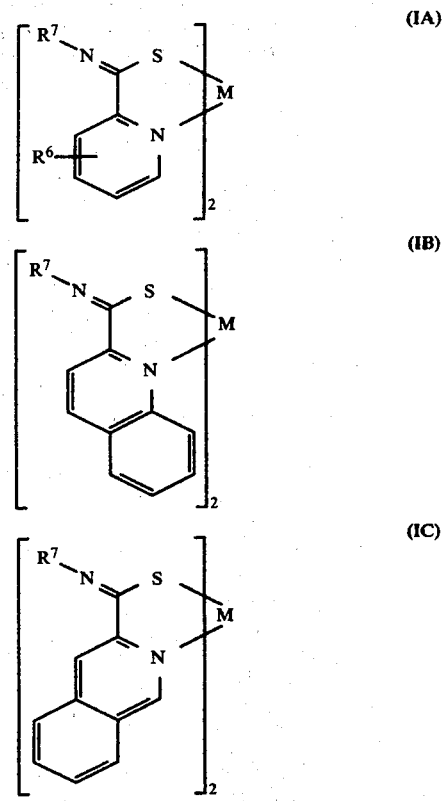

wherein M represents a Cu, Co, Ni, Pd or Pt atom, $R^6$ represents a hydrogen atom, a halogen atom, an alkyl or an aryl group and $R^7$ represents an alkyl or an aryl group.

4. The method of claim 1, wherein said dye is formed by the reaction of a primary aromatic amine color developing agent and a cyan, magenta or yellow dye image forming coupler.

5. The method of claim 4, wherein said yellow dye-forming coupler is a benzoylacetanilide or α-pivalylacetanilide coupler, said magenta dye-forming coupler is a 5-pyrazolone, an indazolone, a pyrazolinobenzimidazole, a pyrazolo-s-triazole or a cyanoacetylcumarone and said cyan dye-forming coupler is a phenol or naphthol coupler.

6. A color photographic material comprising at least one layer containing a photographic dye image wherein said layer or an adjacent layer contains a compound of the formula (I):

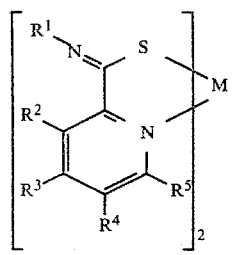
(I)

wherein M represents a Cu, Co, Ni, Pd or Pt atom; $R^1$ represents an alkyl group or an aryl group; $R^2$, $R^3$, $R^4$ and $R^5$ may be the same or different and represent a hydrogen atom, a halogen atom, an alkyl group or an aryl group; and further, $R^2$ and $R^3$, $R^3$ and $R^4$ or $R^4$ and $R^5$ may combine to form a 6-membered ring, said compound of the formula (I) being present in a stabilizing amount for stabilizing said color photographic material against the action of light while not adversely affecting color hue as well as color purity of the color photographic material.

7. The color photographic material of claim 6, wherein said photographic dye image is formed from a color coupler, a DDR coupler, a DRR compound, a dye developer or as a result of a silver dye bleaching process.

8. The color photographic element of claim 6, wherein said dye is formed by the reaction of a primary aromatic amine color developing agent and a cyan, magenta or yellow dye image-forming coupler.

9. The color photographic material of claim 6, wherein said yellow dye-forming coupler is a benzoylacetanilide or α-pivalylacetanilide coupler, said magenta dye-forming coupler is a 5-pyrazolone, an indazolone, a pyrazolinobenzimidazole, a pyrazolo-s-triazole or a cyanoacetylcumarone and said cyan dye-forming coupler is a phenol or naphthol coupler.

10. The color photographic material of claim 6, wherein said compound is represented by the general formula (IA), (IB) or (IC):

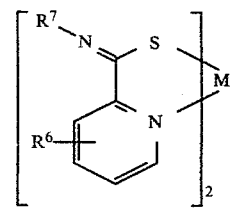
(IA)

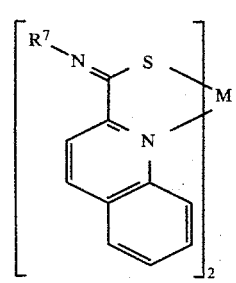
(IB)

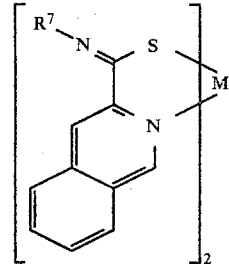
(IC)

wherein M represents a Cu, Co, Ni, Pd or Pt atom, $R^6$ represents a hydrogen atom, a halogen atom, an alkyl or an aryl group and $R^7$ represents an alkyl or an aryl group.

11. The photographic material of claim 8, wherein said photographic dye image is composed of an anthraquinone dye, quinoneimine dye, azo dye, methine dye, polymethine dye, indamine dye, indophenol dye, indigoid dye, carbonium dye, or formazane dyes.

12. A diffusion transfer color photographic material comprising a photosensitive element and an image-receiving element, said image-receiving element, comprising a support having thereon a mordanting layer containing a complex of the formula (I):

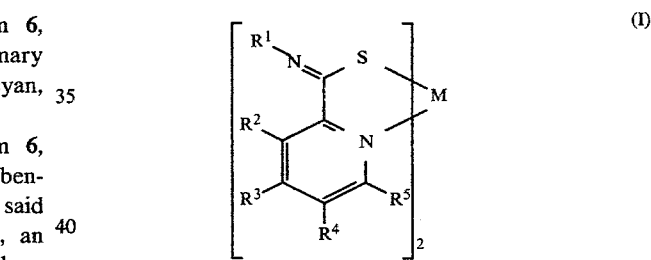
(I)

wherein M represents a Cu, Co, Ni, Pd or Pt atom; $R^1$ represents an alkyl group or an aryl group; $R^2$, $R^3$, $R^4$ and $R^5$ may be the same or different and represent a hydrogen atom, a halogen atom, an alkyl group or an aryl group; and further, $R^2$ and $R^3$, $R^3$ and $R^4$ or $R^4$ and $R^5$ may combine to form a 6-membered ring, said compound of the formula (I) being present in a stabilizing amount to stabilize said diffusion transfer color photographic material against the action of light while not adversely affecting color hue as well as color purity of the diffusion transfer color photographic material.

13. The diffusion transfer color photographic material of claim 12, wherein said compound is represented by the formula (IA), (IB) or (IC):

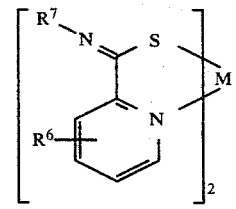
(IA)

-continued
(IB)
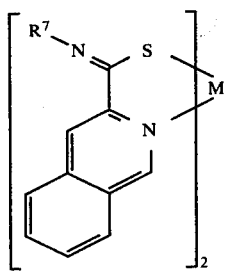
-continued
(IC)
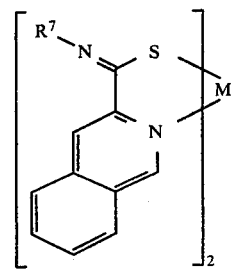
wherein M represents a Cu, Co, Ni, Pd or Pt atom, $R^6$ represents a hydrogen atom, a halogen atom, an alkyl or an aryl group and $R^7$ represents an alkyl or an aryl group.
* * * * *